US011678999B2

(12) United States Patent
Kraus

(10) Patent No.: US 11,678,999 B2
(45) Date of Patent: Jun. 20, 2023

(54) INTERVERTEBRAL IMPLANT, METHOD FOR PRODUCING AN INTERVERTEBRAL IMPLANT, AND METHOD FOR IMPLANTING AN INTERVERTEBRAL IMPLANT

(71) Applicant: Kilian Kraus, Werneck (DE)

(72) Inventor: Kilian Kraus, Werneck (DE)

(*) Notice: Subject to any disclaimer, the term of this patent is extended or adjusted under 35 U.S.C. 154(b) by 188 days.

(21) Appl. No.: 16/705,601

(22) Filed: Dec. 6, 2019

(65) Prior Publication Data

US 2020/0179131 A1 Jun. 11, 2020

(30) Foreign Application Priority Data

Dec. 6, 2018 (EP) .................................... 18210881

(51) Int. Cl.
*A61F 2/44* (2006.01)
*A61F 2/30* (2006.01)

(52) U.S. Cl.
CPC .... *A61F 2/447* (2013.01); *A61F 2002/30156* (2013.01); *A61F 2002/30518* (2013.01)

(58) Field of Classification Search
CPC .................................. A61F 2/44; A61F 2/447
See application file for complete search history.

(56) References Cited

U.S. PATENT DOCUMENTS

| | | | | |
|---|---|---|---|---|
| 6,679,915 | B1 * | 1/2004 | Cauthen | A61F 2/446 623/17.14 |
| 8,043,379 | B2 * | 10/2011 | Moumene | A61F 2/4425 623/17.14 |
| 8,932,356 | B2 | 1/2015 | Kraus | |
| 10,398,566 | B2 | 9/2019 | Olmos et al. | |
| 10,433,977 | B2 | 10/2019 | Lechmann et al. | |
| 2010/0049325 | A1 | 2/2010 | Biedermann et al. | |
| 2011/0029085 | A1 | 2/2011 | Hynes et al. | |
| 2011/0224796 | A1 * | 9/2011 | Weiland | A61F 2/4455 427/2.27 |
| 2013/0158663 | A1 * | 6/2013 | Miller | A61F 2/447 623/17.16 |

FOREIGN PATENT DOCUMENTS

| | | | |
|---|---|---|---|
| WO | 2008070863 | A2 | 6/2008 |
| WO | 2009068021 | A1 | 6/2009 |
| WO | 2009092102 | A1 | 7/2009 |

* cited by examiner

*Primary Examiner* — Christopher J Beccia
(74) *Attorney, Agent, or Firm* — Laurence A. Greenberg; Werner H. Stemer; Ralph E. Locher

(57) ABSTRACT

An intervertebral implant with two opposite contact surfaces configured to bear regionally on vertebral bodies and are spaced apart from each other along a vertical axis and are each arranged on support elements which are adjustable relative to each other. The support elements are guided adjustably relative to each other along a circular arc contour oriented on a longitudinal axis extending perpendicular to the vertical axis in such a way that, by adjustment of the two support elements relative to each other along the circular arc contour, a spacing of the two contact surfaces with respect to the vertical axis and/or an angle setting of the two contact surfaces relative to each other can be predefined and/or modified.

20 Claims, 11 Drawing Sheets

A-A

INTERVERTEBRAL IMPLANT, METHOD FOR PRODUCING AN INTERVERTEBRAL IMPLANT, AND METHOD FOR IMPLANTING AN INTERVERTEBRAL IMPLANT

CROSS-REFERENCE TO RELATED APPLICATION

This application claims the priority, under 35 U.S.C. § 119, of German application EP 18210881, filed Dec. 6, 2018; the prior application is herewith incorporated by reference in its entirety.

BACKGROUND OF THE INVENTION

Field of the Invention

The invention relates to an intervertebral implant, a so-called cage, in particular for use in an anterior lumbar interbody fusion (ALIF), posterior lumbar interbody fusion (PLIF), transforaminal lumbar interbody fusion (TLIF) or extreme lateral interbody fusion (XLIF) operation, in which vertebral bodies are fused. The invention further relates to methods for producing and a method for implanting an intervertebral implant of this kind.

The prior art discloses one-piece and multi-part implants for the spinal column region which are used, for example, in an operation for stiffening the spinal column, in particular for lumbar interbody fusion, i.e. fusion of the vertebral bodies in the region of the lumbar spine. One-piece or solid intervertebral implants generally have the advantage of high mechanical stability. In addition, such implants can be porous or provided with passages in order to allow bone substance to grow through and/or to permit filling with bone substitute material so that the intervertebral implant does not sink in the bone. For example, international patent disclosure WO 2009/068021 A1, corresponding to U.S. Pat. No. 8,932,356, discloses an intervertebral implant with an inner channel structure which promotes incorporation of bone substance.

On account of anatomical differences, in particular as regards the thickness and orientation of the intervertebral disks in the spinal column, an operation for intersomatic or interbody fusion of the vertebrae requires the availability of a large number of one-piece or solid intervertebral implants in different configurations, in most cases about 100 of them. Intervertebral implants of this kind often differ only slightly in terms of their shape, in particular in terms of their vertical or longitudinal extent and/or in terms of the orientation of contact surfaces intended to bear on the vertebral bodies, and it can therefore be difficult for the physician carrying out the treatment to select the implant that is optimally adapted to the implantation.

The aforementioned surgical techniques (ALIF, PLIF, TLIF, XLIF) differ mainly in terms of the type of access route to the spinal column. For example, in the case of a PLIF operation, an intervertebral implant is inserted dorsally, i.e. from the back. On account of the orientation of the vertebrae in the lower lumbar spine in particular, this necessitates the use of approximately wedge-shaped intervertebral implants which, however, on account of the anatomical circumstances, have to be inserted with the broader side first. When using one-piece intervertebral implants, this may pose an increased danger of nerve damage in particular.

To overcome these problems, the prior art has already proposed multi-part, expandable implants which are adjustable in particular in terms of their overall height. For example, international patent disclosure WO 2009/092102 A1, corresponding to U.S. Pat. Nos. 8,551,173, 9,295,562, 9,433,510, 9,597,197 and 10,433,977, describes an expandable intervertebral implant which is variable in particular in terms of its vertical extent. The intervertebral implant is configured to be inserted in the collapsed state, in order to be expanded thereafter to the height of the intervertebral disk substance that has been removed. International patent disclosure WO 2008/070863 A2 corresponding to U.S. Pat. Nos. 8,105,386, 8,568,481, 10,390,963 and 10,398,566, describes a height-adjustable intervertebral implant which, with the aid of a wedge-shaped guide, can be adapted to the size of the intervertebral region that is to be filled.

U.S. patent publication No. 2013/0158663 A1 describes an intervertebral implant with first and second support elements that are provided to bear on vertebral bodies. The support elements can be adjusted relative to each other with the aid of a wedge-shaped component which is arranged between them and which has at least two ramps spaced apart from each other in the axial direction.

The problem with multi-part designs of this kind is firstly that they have to be able to withstand considerable forces, at least until such time as a load-bearing bone structure has grown through the implant. On the other hand, complete growth of bone through currently available multi-part intervertebral implants is often made difficult by the expansion mechanism which is provided for the height adjustment and which can take up a large part of the inner volume that is to be filled with bone substance. Even in the fully incorporated state, the load-bearing capacity obtained is often insufficient.

SUMMARY OF THE INVENTION

The object of the invention is to make available an intervertebral implant which is variably adaptable in terms of its geometric shape and in particular has a high degree of mechanical stability.

This object is achieved by an intervertebral implant having the features of the independent claim.

Advantageous embodiments are the subject matter of the dependent claims.

An intervertebral implant (also called a cage) has two opposite contact surfaces which are configured to bear at least regionally on vertebral bodies and are spaced apart from each other along a vertical axis. The contact surfaces are each arranged on support elements which are adjustable relative to each other and which are guided adjustably relative to each other along a circular arc contour oriented on a longitudinal axis extending perpendicular to the vertical axis in such a way that, by adjustment of the two support elements relative to each other along the circular arc contour, a spacing of the two contact surfaces with respect to the vertical axis and an angle setting of the two contact surfaces relative to each other and with respect to the vertical axis can be predefined and/or modified.

The statement that the two support elements are adjustable relative to each other along a circular arc contour is to be understood in particular as meaning that the two support elements are guided displaceably along the circular arc contour and can be locked relative to each other at least at predefined positions. Preferably, the two support elements can be locked relative to each other at any desired position. The locking can be releasable (reversible) or non-releasable (irreversible).

The statement that the circular arc contour is oriented along a longitudinal axis extending perpendicular to the vertical axis is to be understood in particular as meaning that the curvature of the circular arc contour extends in a plane which is parallel to the plane spanned by the vertical axis and the longitudinal axis. In some embodiments, the vertical axis is identical for example to the central vertical axis of the intervertebral implant, and the longitudinal axis is identical in particular to the central longitudinal axis of the intervertebral implant.

Since the two support elements are adjustable relative to each other along the circular arc contour, which is oriented along the longitudinal axis of the intervertebral implant, an adjustment of the two support elements relative to each other effects not only a variation in the longitudinal extent in general, but also a change in the vertical extent, i.e. a change in the spacing between the two opposite contact surfaces, and also a change in the angle at which the contact surfaces are arranged relative to each other. This allows the same intervertebral implant to be used for different implantation sites. In particular, in the context of intersomatic or interbody fusion of the vertebrae, the intervertebral implant according to the invention can be flexibly adapted to the spacing and the orientation of the two vertebral bodies that are to be bridged or fused. As a result of this, the number of intervertebral implants that have to be made available for an operation of this kind can be greatly reduced, which ultimately also makes it easier for the treating physician to select the intervertebral implant best adapted to the implantation site.

The circular arc contour can extend differently in different embodiments of the intervertebral implant. In particular, variations are possible in terms of the radius of curvature and/or the inclination of the circular arc contour with respect to the longitudinal axis and/or the vertical axis of the intervertebral implant. The curvature and inclination of the circular arc contour define in particular how far a change in length of the intervertebral implant is associated with a change in the vertical extent or the orientation (or angle setting) of the contact surfaces relative to each other. Provision is made that variants of the intervertebral implant according to the invention, differing in particularly in this regard, are made available to the treating physician during the operation.

Adjustment of the two support elements brings about a variation in the length of the intervertebral implant in the direction of the longitudinal axis and/or a variation in the height or thickness of the intervertebral implant in the direction of the vertical axis and/or a variation in the orientation of the two contact surfaces relative to each other. In typical embodiments and designs of the intervertebral implant and in particular of the profile of the circular arc contour, the length of the intervertebral implant is approximately between 15 mm and 45 mm, preferably approximately between 20 mm and 40 mm, i.e. the length can vary at most by approximately 30 mm, preferably by approximately 20 mm. Accordingly, the thickness (or also height) of the intervertebral implant in typical designs is between 4 mm and 22 mm, preferably between 6 mm and 20 mm, i.e. the variation in the direction of the vertical axis is at most approximately 18 mm, preferably approximately 14 mm. The contact surfaces extend parallel to the longitudinal axis or run by up to ±15° with respect to the longitudinal axis. Accordingly, in typical embodiments, the maximum variation in the orientation of the two contact surfaces relative to each other is approximately 30°.

The circular arc contour has in particular a constant radius of curvature. Such a configuration has the effect that the two support elements always bear closely on each other along the circular arc contour. This is particularly advantageous in order to compensate for considerable forces acting in the direction of the vertical axis.

The intervertebral implant is intended in particular to be inserted into a region located between two vertebral bodies in such a way that the vertical axis is oriented in the direction of the longitudinal axis of the spinal column. By an adjustment of the two support elements along the circular arc contour, the extent of the intervertebral implant in particular in the direction of the longitudinal axis of the spinal column can be adapted to the height of the intervertebral disk substance that is to be replaced. In addition, the adjustment of the two support elements relative to each other brings about a change of the contact surfaces arranged opposite each other. The inclination of the two contact surfaces is preferably adapted to the orientation of the two adjacent vertebral bodies in such a way that the latter bear on the respective contact surfaces over as large a region as possible.

Since the intervertebral implant is variable in terms of its overall height, i.e. in terms of its extent in the direction of the vertical axis, it is possible in particular to minimize the overall height prior to insertion, such that only very small access routes are needed for the implantation. The adaptation of the spatial configuration of the intervertebral implant, in particular of the spacing and/or the orientation of the contact surfaces relative to each other by adjustment of the two support elements to the anatomical circumstances of the implant, can in particular be carried out after the insertion into the human body.

The intervertebral implant is configured for example as a bone-connecting or bone-bridging implant. This means in particular that at least one contact surface of the intervertebral implant comes directly into contact at least in some regions with a bone, for example with a vertebral body. The contact surfaces are thus intended to be in direct contact with bone substance, in particular with vertebral bodies, and for this purpose they have for example a suitable roughness and/or a structuring, for example a corrugated or toothed surface structuring. Alternatively or additionally, the contact surfaces are porous, in particular with open pores, in order to permit inward growth of bone substance. In other embodiments, the contact surfaces are substantially smooth.

In some embodiments, the movement of the two support elements relative to each other is limited to the degree of freedom of movement directed tangentially to the circular arc contour. This can be effected, for example, by suitable guides, which if appropriate have undercuts. In some embodiments, one support element has, for example, at least one groove, which extends over at least a portion of the circular arc contour. The other support element accordingly has at least one projection, which is guided displaceably inside the at least one groove.

Intervertebral implants configured to fuse with bone substance (natural bone substance) or to be filled with bone substitute material (artificial bone substance) preferably have a hollow space or a plurality of hollow spaces, particularly in the region between the opposite contact surfaces.

In preferred embodiments, at least one of the support elements contains an inner structure with a multiplicity of channels which are open to the contact surface. The inner structure (channel structure) extends into the interior of the intervertebral implant from the contact surface bearing on the bone. The channels each have a cross-sectional area of 8,000 $\mu m^2$ to 7,000,000 $\mu m^2$, preferably a cross-sectional area of 50,000 $\mu m^2$ to 3,100,000 $\mu m^2$, particularly preferably a cross-sectional area of 125,000 $\mu m^2$ to 570,000 $\mu m^2$. A channel structure of such dimensions is adapted to the capillary action of blood and thus promotes entry of blood to a sufficient depth. This advantageously supports the fusion of the intervertebral implant to adjoining bone, in particular to vertebral bodies.

In some embodiments, both contact surfaces arranged opposite each other are provided with inner structures which each comprise a multiplicity of channels. The inner structures arranged opposite each other form, in at least one part of the intervertebral implant, at least one hollow space which is continuously open in the direction of the vertical axis. Such configurations thus promote the at least partial but preferably complete permeation of the intervertebral implant with natural bone substance or the at least partial but preferably complete filling of the intervertebral implant with artificial bone substance.

In illustrative embodiments, the inner structures formed by the channels extend over the entire extent of the respective support element in the direction of the vertical axis. For example, the channels substantially extend at least partially or completely parallel to the vertical axis. The statement that the channels extend substantially parallel to the vertical axis is to be understood in particular as meaning that the adjustment of the two support elements relative to each other entails a slight change in the orientation of the channels. Depending on the relative position of the two support elements with respect to each other, the channels introduced into the respective support elements can be offset in relation to each other. The channels or channel structures preferably overlap each other in such a way that the hollow space formed is continuously open in the direction of the vertical axis. It has proven advantageous here if the thickness of channel walls separating contiguous channels is considerably smaller than the diameter, particularly, in the case of channels of non-round cross section, the average diameter of the channels. For example, the average diameter of the channels is 2 to 4 times the thickness (channel wall thickness) of the channel walls.

In some embodiments, the inner structure is honeycomb-shaped, lattice-shaped or mesh-shaped. Such configurations permit the penetration of natural bone substance and/or the introduction of bone substitute material and can be exposed to high mechanical loads.

In some embodiments, the channels have a round or oval cross section or a cross section in the shape of a polygon, in particular a regular polygon, for example a triangular, rectangular, square or hexagonal cross section. The inner structure is in particular configured in a honeycomb shape, a lattice shape or mesh shape by several such channels. In particular, channel structures that are formed by channels with a polygonal cross section have a high degree of mechanical stability.

In some embodiments, at least one of the support elements has at least one cavity which forms an opening on the contact surface of the at least one support element, the surface of which opening extends at least over 1/10 and at most 3/4 of the contact surface of the at least one support element. The cavity serves, for example, to permit penetration of natural bone substance or filling of the intervertebral implant with artificial bone substance or bone substitute material. The opening of the cavity and/or the cross-sectional area thereof can be of any desired shape and is, for example, round or oval.

In some embodiments, both contact surfaces arranged opposite each other are each provided with at least one cavity, the cavities being arranged opposite each other in such a way that the cavities in at least one part of the intervertebral implant form at least one continuous hollow space in the direction of the vertical axis. The size of the continuous hollow space in the direction of the vertical axis can in particular depend on the arrangement of the two support elements relative to each other.

In further embodiments, both support elements have an inner structure with a plurality of channels and also at least one cavity, which form a continuous hollow space in the direction of the vertical axis. In other illustrative embodiments, one support element has at least one relatively large cavity, and the other support element has an inner structure with a plurality of relatively small channels. In this way, a hollow space that is continuous in the direction of the vertical axis can be created in at least one part of the intervertebral implant.

The contact surfaces can be plane or can have a curvature. In some embodiments, at least one of the contact surfaces has a convex bulge. Preferably, both opposite contact surfaces bulge outward in a convex shape.

In some embodiments, the two support elements having the contact surfaces are adjustable and/or lockable relative to each other by a reversible or irreversible adjustment mechanism. Reversible adjustment mechanisms are particularly advantageous if the implant subsequently has to be removed, for example because of complications or incompatibility. Reversible (releasable) adjustment mechanisms can be, for example, adjusting screws or the like. Irreversible adjustment mechanisms, for example latch connections or the like, generally have the advantage of being simple to produce. In addition, a return movement of the support elements relative to each other, in particular under an axial load in the direction of the longitudinal axis of the spinal column, can be efficiently suppressed.

In one embodiment, the reversible adjustment mechanism is preferably configured as a helical gear and has a threaded spindle guided in a thread. A helical gear of this kind with threaded spindle is self-locking, i.e. an axial load acting in the direction of the vertical axis or in the direction of the longitudinal axis of the spinal column generates a shearing moment which acts on the threaded spindle guided substantially along the circular arc contour in particular, which blocks the threaded spindle and thus counteracts a return movement of the mutually adjusted support elements. Moreover, the orientation of the circular arc contour with respect to the vertical axis generates a shearing moment acting on the threaded spindle, under an axial load acting in the direction of the vertical axis. It is thus possible to efficiently counteract a return movement of the two mutually adjusted support elements on account of forces acting along the longitudinal axis of the spinal column. In addition, a helical gear of this configuration takes up only relatively little installation space, such that a large part of the volume of the intervertebral implant, for example approximately 50% or more, can be continuously open in order to allow the above-described fusion with bone substance. In order to adjust the two support elements relative to each other, an implantation tool, for example similar to a screw driver or hexagon key, is inserted into the intervertebral implant and moves the threaded spindle in rotation.

In some embodiments, the thread is introduced in one, in particular just one, of the two support elements and has a curvature corresponding to the curvature of the circular arc contour. In this way, a reversible adjustment mechanism is provided which permits a continuous adjustment of the two support elements relative to each other along the circular arc contour. For example, the thread extends over approximately 50% of the longitudinal extent of the intervertebral implant in the direction of the longitudinal axis. The thread is introduced in the inner face of the support element and is for example configured in one piece with the latter. In other embodiments, the thread is firstly manufactured as a separate part and is then connected to the support element in particular by conventional joining techniques.

In one embodiment, the threaded spindle is optionally insertable into a spindle seat that inhibits a rotation movement. For this purpose, the threaded spindle can have, for example at one end, a portion which has a non-rotationally symmetrical cross section and which is insertable, in particular with form-it engagement, into a spindle seat of suitably complementary shape. For example, the threaded spindle can be pushed out of the spindle seat with the aid of the aforementioned implantation tool, in order to permit an adjustment of the two support elements relative to each other.

In some embodiments, a reversible or irreversible adjustment mechanism is provided which is configured in particular as a latch mechanism. For this purpose, the two support elements can for example be provided, on mutually facing sides, with complementary latch grooves, latch teeth or the like, which permit locking of the two support elements at predefined positions.

In some embodiments of the latch mechanism, one of the support elements contains at least one deflectable latch arm, and the other of the support elements contains a plurality of latch grooves spaced apart from each other along the circular arc contour. The at least one deflectable and in particular resilient latch arm is configured to latch into the latch grooves in order to lock the support elements.

In some embodiments, a lateral outer jacket of the intervertebral implant is solid and in particular has no openings. Such embodiments provide increased mechanical stability.

In preferred embodiments, the intervertebral implant is made partially, preferably completely, of a metal, a metal alloy, in particular a titanium alloy, or a plastic, in particular polyether ketone. Of particular preference are so-called grade 5 alloys, in particular Ti-6Al-4V, which is distinguished by high strength and durability. In other embodiments, the metal or the metal alloy is made of titanium, zirconium, oxidized zirconium, hafnium, platinum, rhodium, niobium, medical-grade stainless steel, cobalt-chromium-steel or tantalum. Non-metallic materials from which the intervertebral implant can be manufactured include fiber-reinforced plastics, for example glass and/or carbon fibers embedded in a matrix.

In preferred embodiments, the intervertebral implant is configured as a cervical, thoracic or lumbar cage, in particular an ALIF cage, PLIF cage or TLIF cage, or as an artificial intervertebral disk or as an implant for the fusion of vertebrae.

The intervertebral implant described above can be produced, for example, using conventional, in particular subtractive production methods. In this connection, consideration may be given to milling or other subtractive manufacturing techniques, in particular laser cutting and/or laser ablation. On account of the complex geometry of the intervertebral implant, the latter in preferred embodiments is produced by means of a generative production method (additive production, 3D printing), in particular by selective laser melting, selective laser sintering, electron beam melting or fused filament fabrication. By using generative manufacturing techniques such as these, it is in particular ensured that the support elements are formed from one piece. In this way, it is possible in particular to avoid mechanical weak points, which can arise for example during the subsequent assembling of multi-part components.

Other features which are considered as characteristic for the invention are set forth in the appended claims.

Although the invention is illustrated and described herein as embodied in an intervertebral implant, a method for producing an intervertebral implant, and a method for implanting an intervertebral implant, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Parts that correspond to each other are provided with the same reference signs in all of the figures.

FIGS. 1 to 15 illustrate purely by way of example, and in a non-limiting manner, a first illustrative embodiment of a intervertebral implant 100 according to the invention.

Figure 1:
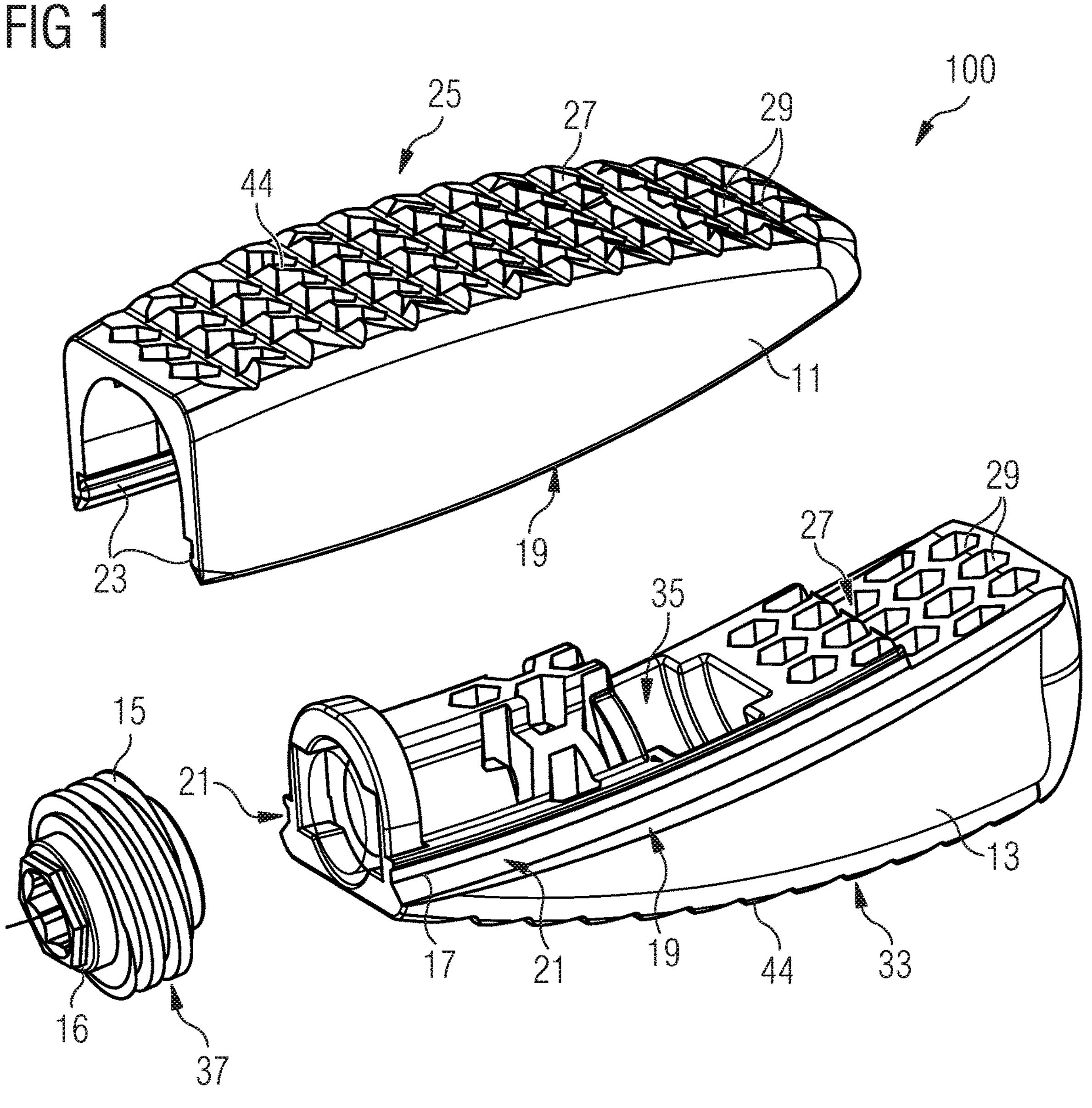
FIG. 1 is a diagrammatic, exploded, perspective view of a multi-part intervertebral implant according to a first illustrative embodiment.
Figure 2:
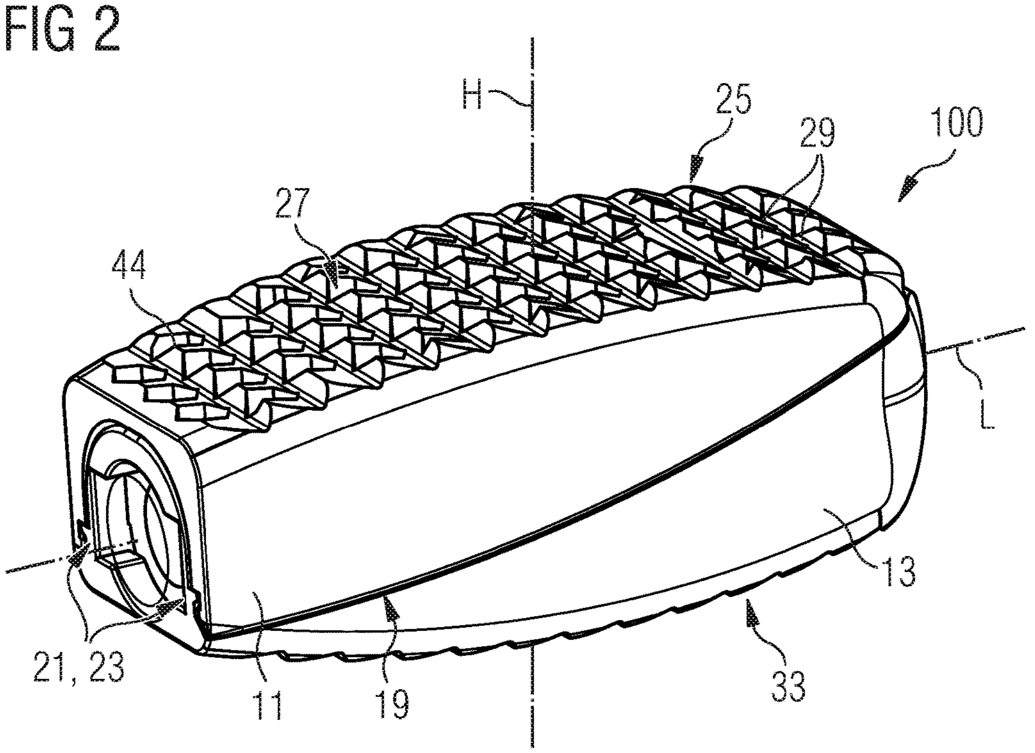
FIG. 2 is a perspective view of the intervertebral implant from FIG. 1 locked in a first position.
Figure 3:
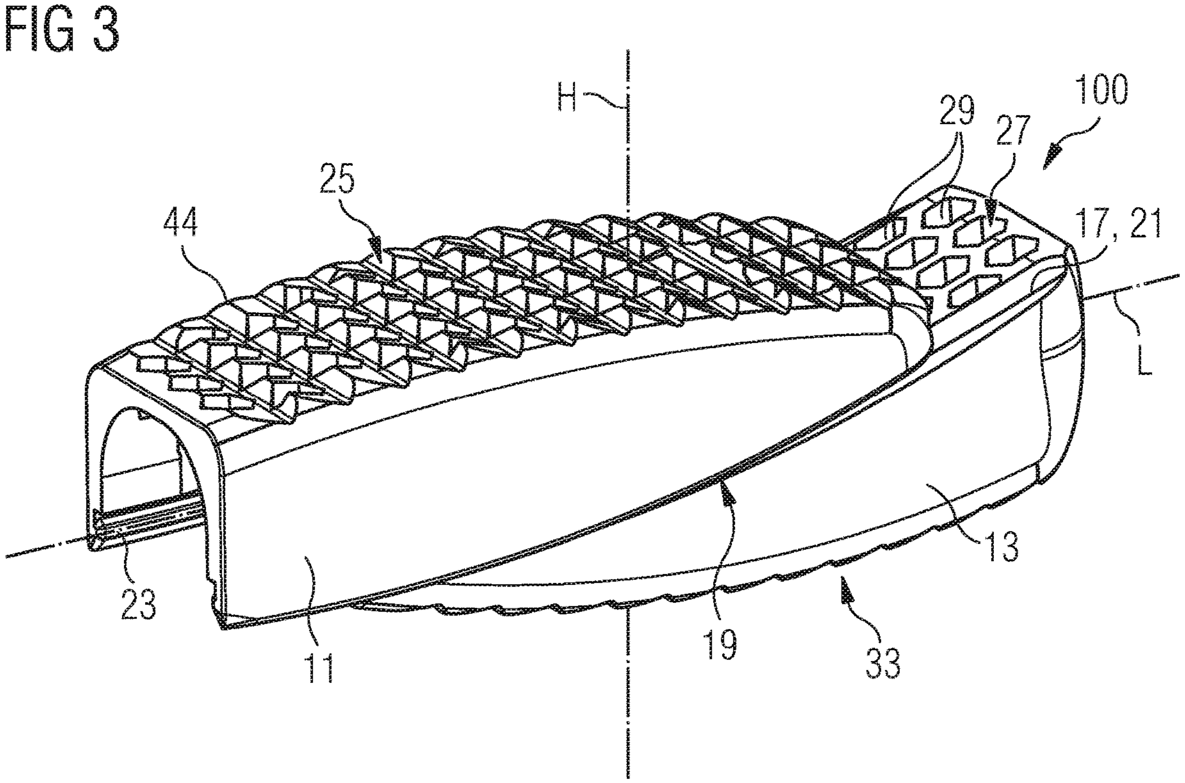
FIG. 3 is a perspective view of the intervertebral implant from FIG. 1 locked in a second position.
Figure 4:
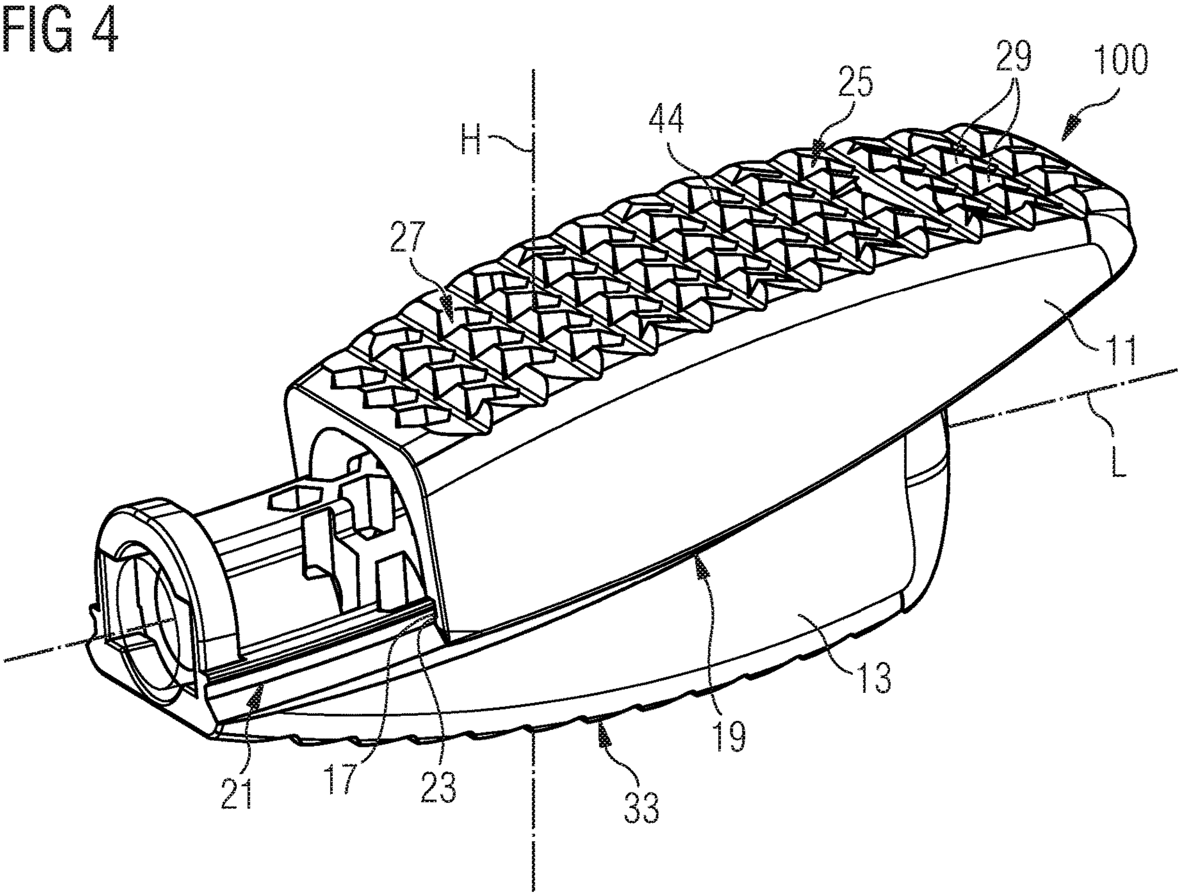
FIG. 4 is a perspective view of the intervertebral implant from FIG. 1 locked in a third position.
Figure 5:
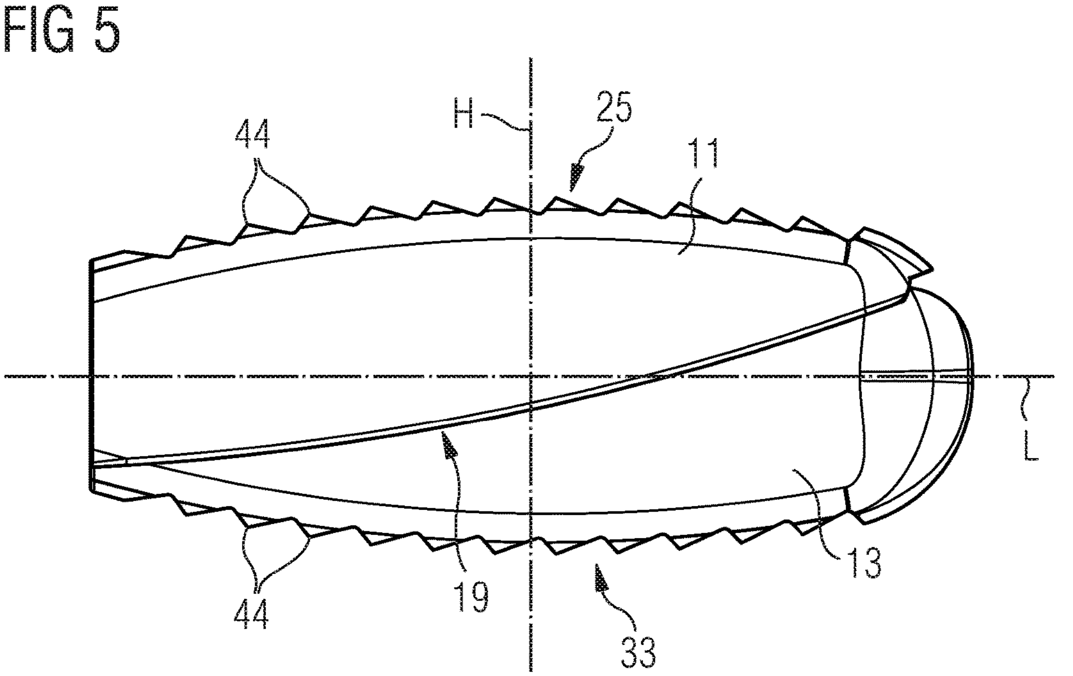
FIG. 5 is a side view of the intervertebral implant according to the first illustrative embodiment locked in the first position.
Figure 6:
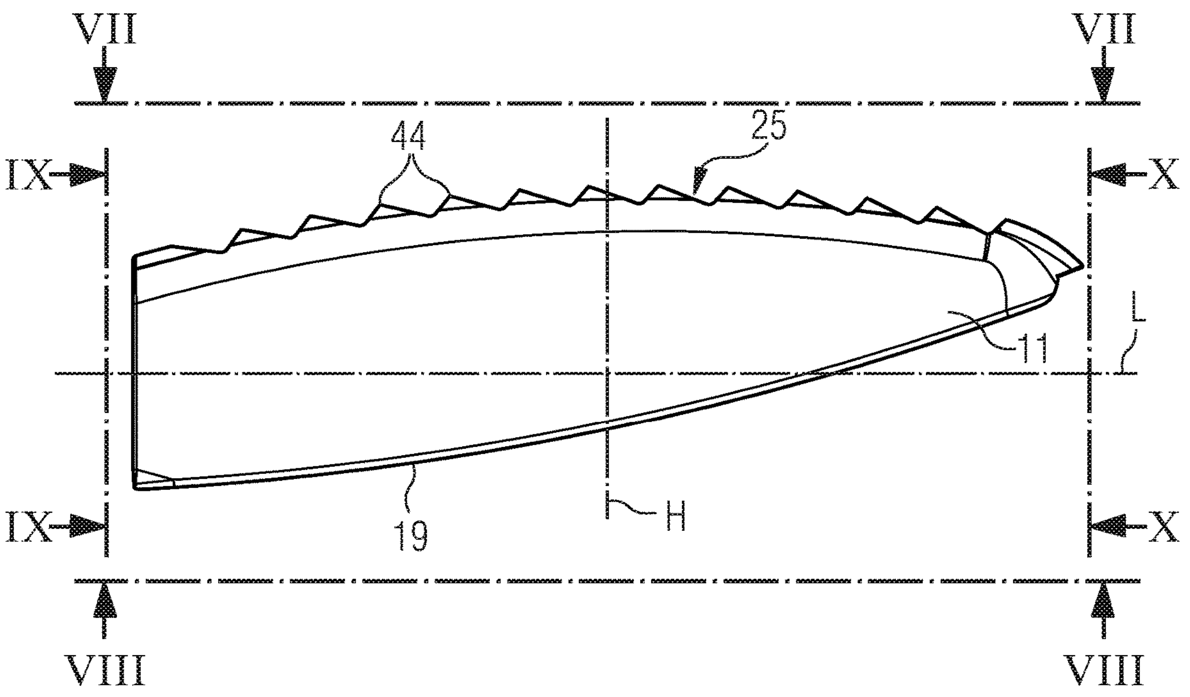
FIG. 6 is a side view of a first support element of the intervertebral implant according to the first illustrative embodiment.
Figure 7:
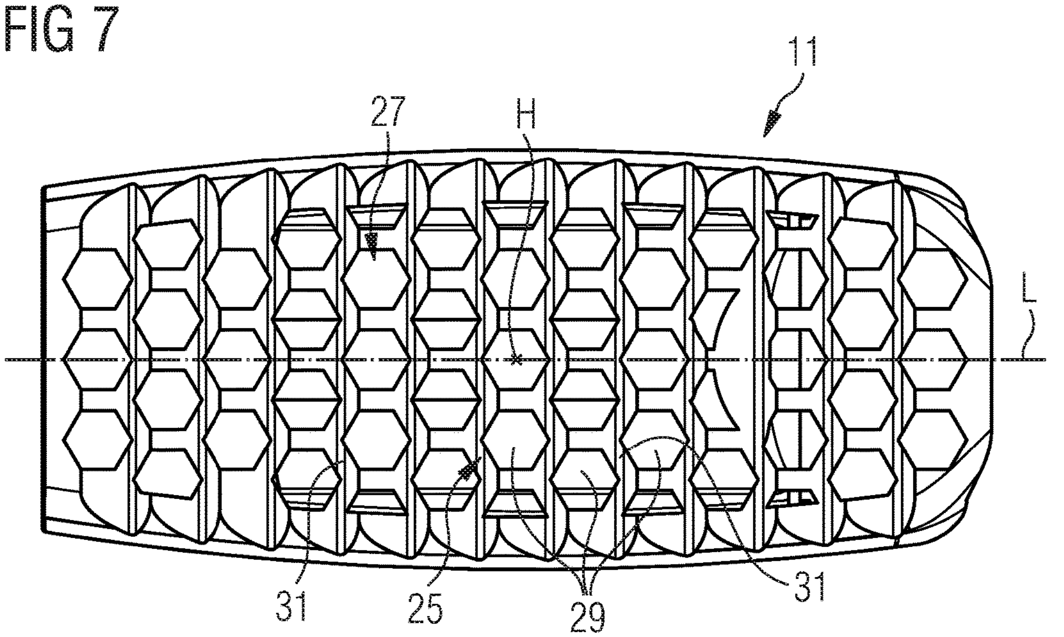
FIG. 7 is a plan view of a contact surface of the first support element from FIG. 6.
Figure 8:
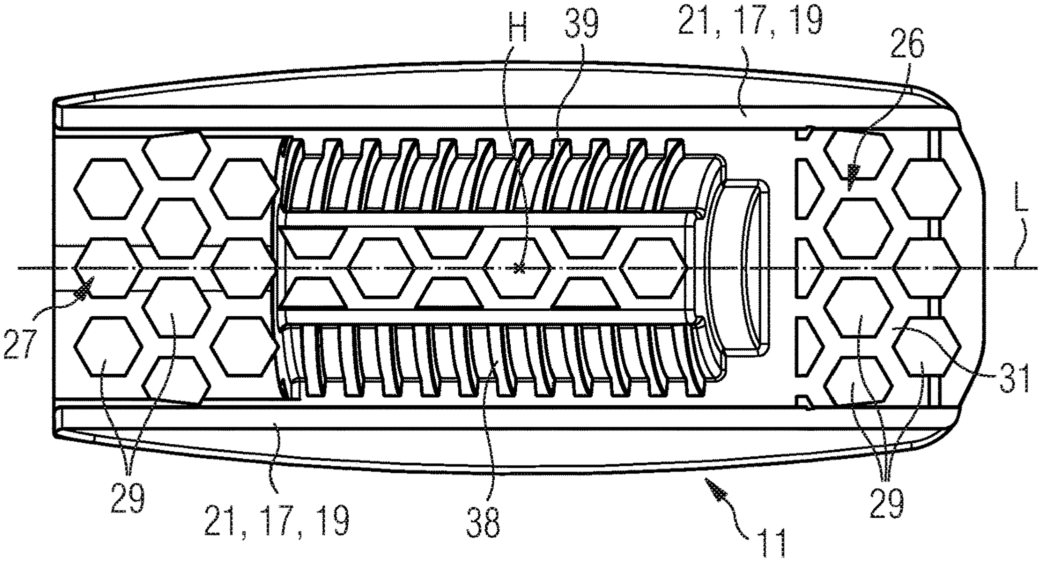
FIG. 8 is a plan view of an inner face of the first support element from FIG. 6.
Figure 9:
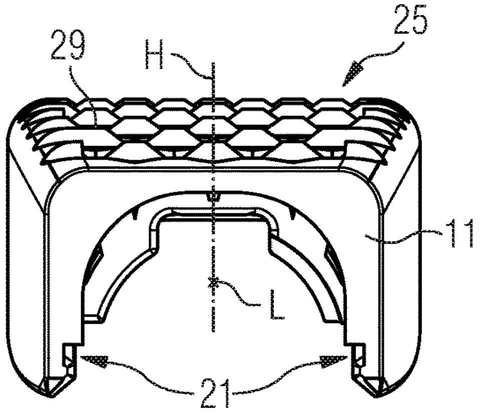
FIG. 9 is a perspective view of the first support element from FIG. 6 in a plan view along the longitudinal axis.
Figure 10:
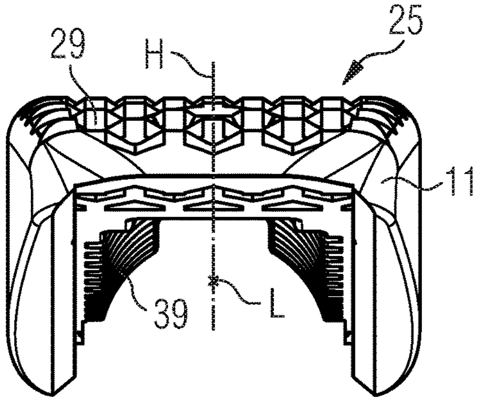
FIG. 10 is a perspective view of the first support element from FIG. 6 in a further plan view along the longitudinal axis.
Figure 11:
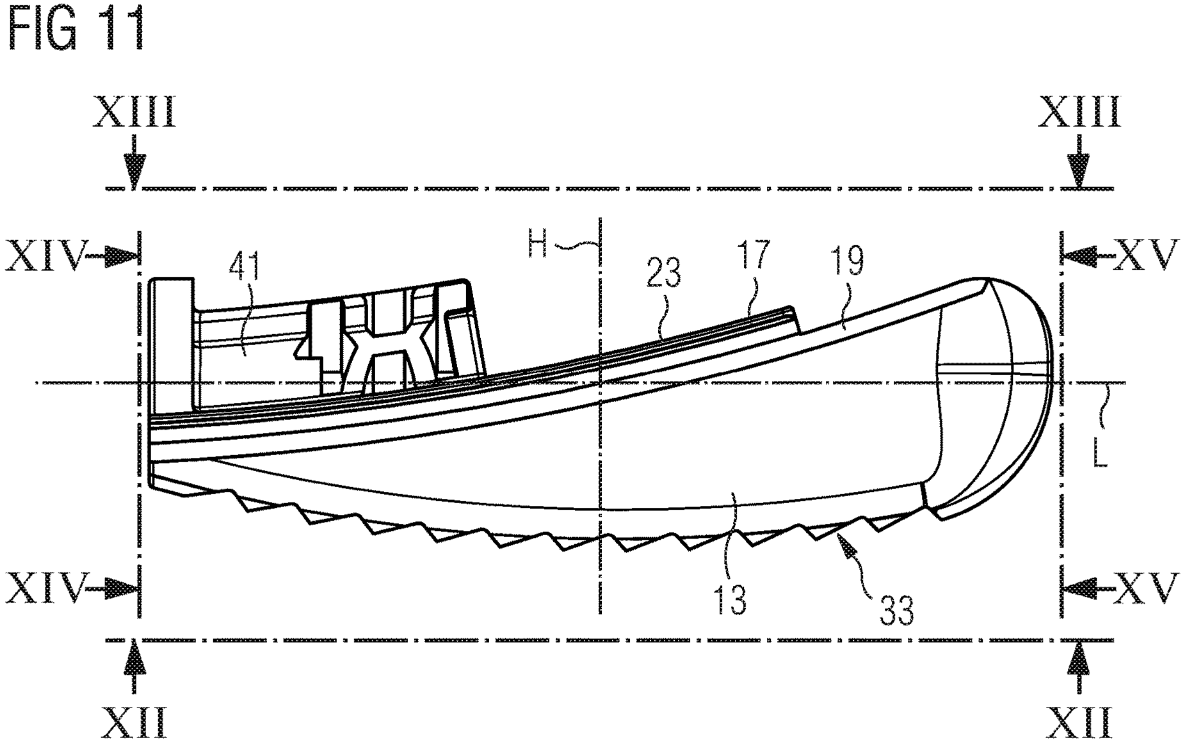
FIG. 11 is a side view of a second support element of the intervertebral implant according to the first illustrative embodiment.
Figure 12:
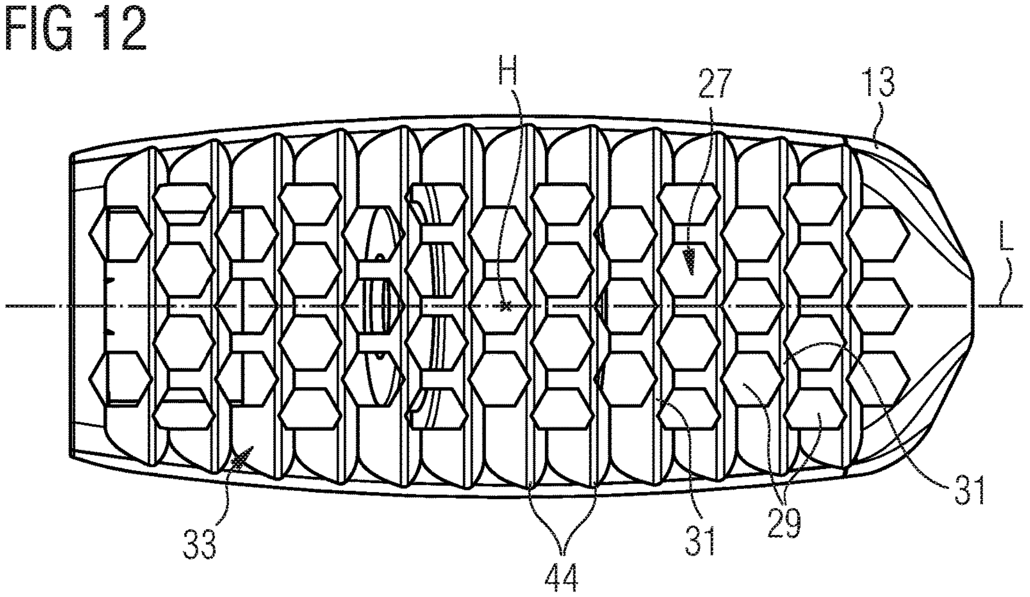
FIG. 12 is a plan view of a contact surface of the second support element from FIG. 11.

Referring now to the figures of the drawings in detail and first, particularly to FIG. 1 thereof, there is shown the multi-part intervertebral implant 100 according to the first illustrative embodiment in an exploded view. The intervertebral implant 100 contains three components: A first support element 11, a second support element 13, and a threaded spindle 15. In the first illustrative embodiment, these three components 11, 13, 15 are each configured in one piece. In alternative embodiments, these components 11, 13, 15 can also each be formed from several component parts that have been joined together in a final manufacturing step.

The support elements 11, 13 essentially determine the external physical shape of the intervertebral implant 100, which shape is variable. For this purpose, the first and the second support element are mounted displaceably relative to each other along a guide 17. The guide 17 extends along a circular arc contour 19 in such a way that, by adjustment of the two support elements 11, 13 relative to each other, their orientation with respect to a longitudinal axis L and a vertical axis H, the longitudinal extent of the intervertebral implant 100 along the longitudinal axis L and the vertical extent in the direction of the vertical axis H can be modified. This is illustrated in a particularly schematic manner in the perspective view in FIGS. 2 to 4. In order to permit such functionality, the curvature of the circular arc contour 19 extends in the plane spanned by the vertical axis H and the longitudinal axis L or in a plane extending parallel to the plane. This can be seen in particular from the side view in FIG. 5 for example.

The guide 17 contains two grooves 21 which extend along the circular arc contour 19 and are introduced on laterally opposite sides of the second support element 13. Correspondingly, the first support element 11 has projections 23 which have shapes complementing the grooves 21 and which engage in said grooves in the final assembled state (cf. in particular FIGS. 2 to 4). In this way, the movement of the two support elements 11, 13 relative to each other is limited to a relative displacement along the circular arc contour 19.

The shape of the first support element 11 can be seen best from FIGS. 6 to 10. The first support element 11 has a first contact surface 25 which is provided to bear directly, at least in some regions, on a vertebral body in the implanted state. As can be seen in particular from FIG. 5 or 6, the first contact surface 25 has a toothed or corrugated surface structuring with a plurality of ribs 44 extending parallel to each other. As an alternative to this, the first contact surface 25 can also be smooth.

The second support element 13, which is shown in detail in FIGS. 11 to 15, has a second contact surface 33 which, in terms of its physical shape, substantially corresponds to the first contact surface 25 and is likewise provided to bear on a vertebral body.

The contact surfaces 25, 33 of the first illustrative embodiment are convex, i.e. they each bulge outward. As an alternative to this, the first and/or second contact surface 25, 33 can also be plane, i.e. flat.

The first support element 11 moreover forms a portion of an inner structure 27 which extends in the direction of the vertical axis H through the entire intervertebral implant 100 and is formed by a multiplicity of channels 29 lying alongside each other. The portions of the channels 29 introduced inside the first support element 11 form an open channel structure which is open both to the first contact surface 25 and also to a first inner face 26 (cf. in particular FIG. 8) of the first support element 11.

The second support element 13 forms a further portion of the inner structure 27 and for this purpose likewise has inner channels 29 of hexagonal cross section, which extend along the vertical axis H through the second support element 13. The portions of the channels 29 that extend through the second support element 13 are correspondingly likewise open to the second contact surface 33 and to the second inner face 34 of the second support element 13.

The inner structure 27 formed by the channels 29 of the first and second support element 11, 13 forms a structure that is open at least in some regions in the direction of the vertical axis H in order to promote fusion of the intervertebral implant 100 to bone substance or to promote filling with artificial bone substitute material. The inner structure 27 in the direction of the vertical axis H is advantageously also ensured during an adjustment of the two support elements 11, 13 relative to each other (cf. in particular FIGS. 2 to 4). Channel walls 31 which laterally delimit the channels 29 have a wall thickness that is much smaller than the average diameter of the channels 29. This has the effect that the channel structures introduced into the first and the second support element 11, 13 at least partially overlap for different settings of the support elements 11, 13 relative to each other and thus make available fluidic connections between the contact surfaces 25, 33.

In the first illustrative embodiment, shown purely by way of example, the channels 29 have substantially a hexagonal symmetry and, accordingly, the inner structure 27 is substantially honeycomb-shaped.

In alternative embodiments, the inner structure 27 can be configured differently. In particular, it can vary in almost any desired way in terms of the geometry and arrangement of the channels 29. However, it is advantageous if at least most of the channels 29 extend through the entire intervertebral implant 100, so that the latter can have bone substance grow almost completely through it or can be filled with bone substitute material.

The open channels 29 each have a cross-sectional area of 8,000 $\mu m^2$ to 7,000,000 $\mu m^2$, preferably a cross-sectional area of 50,000 $\mu m^2$ to 3,100,000 $\mu m^2$, particularly preferably a cross-sectional area of 125,000 $\mu m^2$ to 570,000 $\mu m^2$.

Channels 29 of such dimensions promote the entry of blood to a sufficient depth into the inner structure 27 formed by the channels 29, in order thereby to promote the fusion of the implant to the adjoining bones, in particular vertebral bodies.

Figure 13:
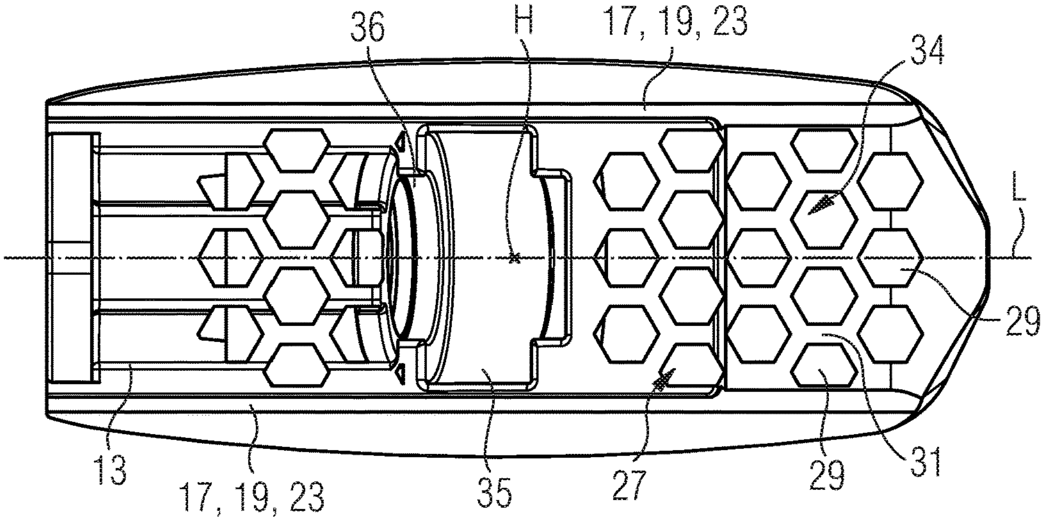
FIG. 13 is a plan view of an inner face of the second support element from FIG. 11.
Figure 14:
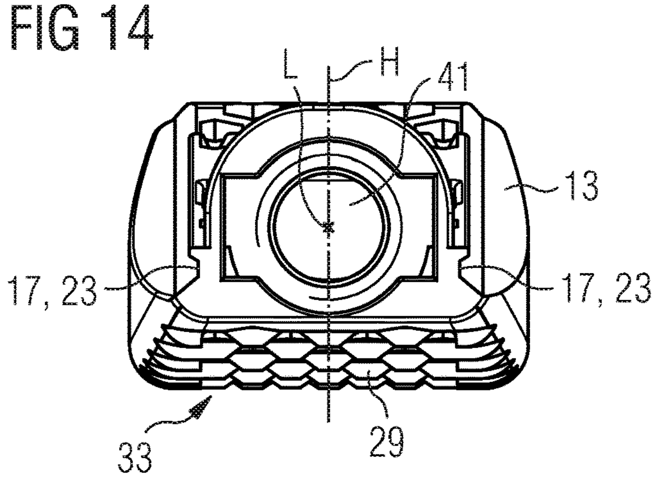
FIG. 14 is a perspective view of the second support element from FIG. 11 in a plan view along the longitudinal axis.
Figure 15:
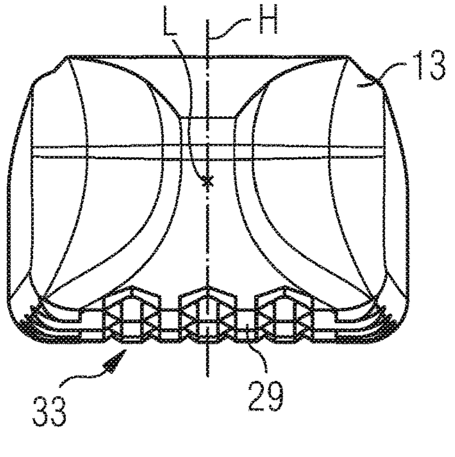
FIG. 15 is a perspective view of the second support element from FIG. 11 in a further plan view along the longitudinal axis.

The threaded spindle 15 is inserted into a recess 35 which is introduced approximately centrally in the second support element 13 (cf. in particular FIG. 13). The outer thread 37 of the inserted threaded spindle 15 engages in a thread 39 which is provided with a corresponding inner thread 38 and which is introduced into the first support element 11 (cf. in particular FIG. 8). In the embodiment shown purely by way of example and to be understood as non-limiting, the thread 39 extends over approximately 50% of the axial length of the intervertebral implant 100.

The inserted threaded spindle 15 can be moved in rotation by an inserted implantation tool for adjusting the two support elements 11, 13. The second support element 13 is provided with an elongate insertion opening 41 for insertion of the implantation tool, which opening extends substantially axially in the direction of the longitudinal axis L.

In alternative embodiments, the recess 35 for receiving the threaded spindle 15 and also the thread 39 are arranged offset to one end along the longitudinal axis.

The position of the threaded spindle 15 with respect to the second support element 13 is fixed by the recess 35, if appropriate except for a predefined play. During a rotation of the threaded spindle 15, the latter runs along the thread 39, such that the first support element 11 is displaced relative to the second support element 13 along the circular arc contour 19.

The thread 39 has a curved shape. In particular, the curvature of the thread 39 corresponds to that of the circular arc contour 19. The curved contour of the thread 39 thus runs in particular parallel to the circular arc contour 19.

The threaded spindle 15 can at one end have an outer contour 16 (cf. in particular FIG. 1) which has no continuous rotational symmetry and is provided to be inserted into a spindle seat 36 of complementary shape (cf. in particular FIG. 13) in order thereby to inhibit an unwanted rotation movement of the threaded spindle 15. The spindle seat 36 is at the end of the recess 35 and receives, with form-fit engagement, the end of the threaded spindle 15 with the outer contour 16, in order in particular to at least substantially avoid a return movement of the mutually adjusted support elements 11, 13 under an axial load acting in the direction of the longitudinal axis of the spinal column. The outer contour of the threaded spindle 15 and the spindle seat 36 are expediently configured to complement each other and are not rotationally symmetrical. In the embodiment shown purely by way of example and to be understood as non-limiting, the outer contour 16 has the shape of a hexagon insert and the spindle seat 36 the shape of a hexagon socket. Other physical configurations are possible and lie within the scope of the invention.

The threaded spindle 15 and the spindle seat are designed in such a way that the threaded spindle 15 can be guided or pushed out of the spindle seat 36 by means of an implantation tool, such that the threaded spindle 15 can be rotated in order to adjust the two support elements 11, 13 relative to each other.

Figure 16:
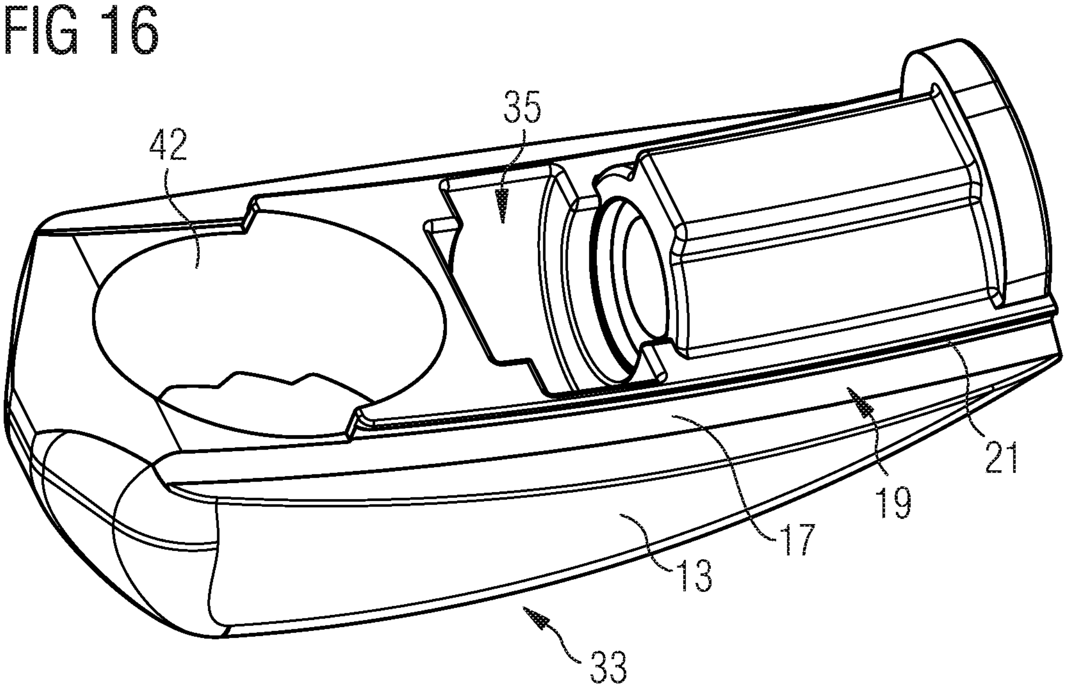
FIG. 16 is a perspective view of the support element in a second illustrative embodiment.
Figure 17:
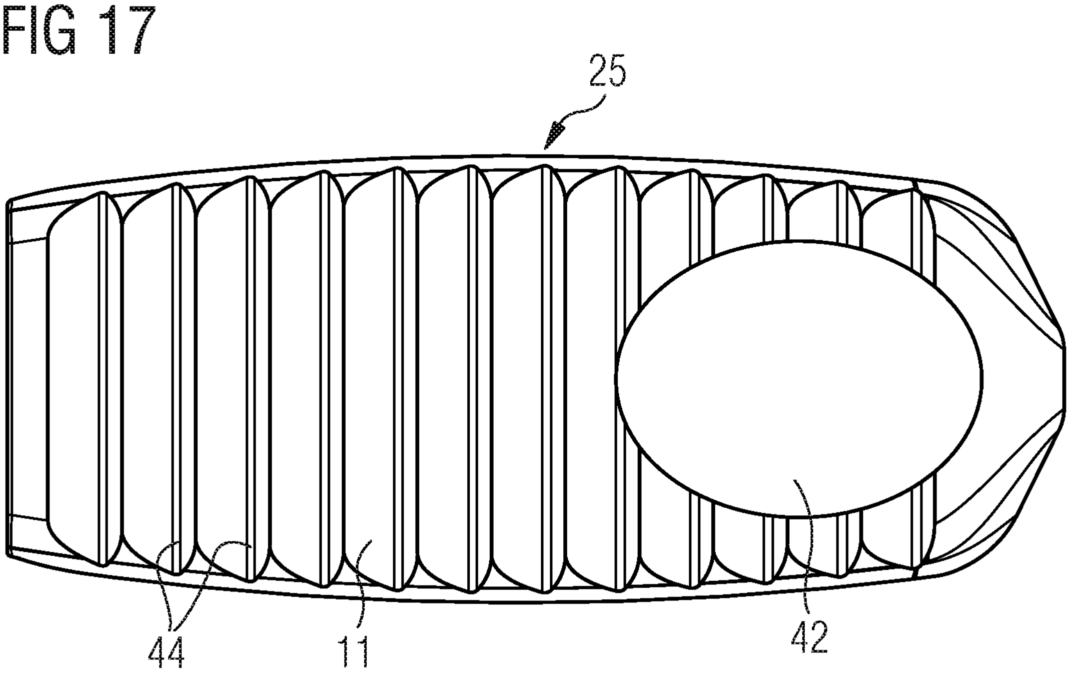
FIG. 17 is a plan view of the support element of the second illustrative embodiment.

FIGS. 16 and 17 show a possible embodiment of the intervertebral implant 100. FIG. 16 shows an alternative embodiment of the second support element 13 in a perspective view. FIG. 17 shows an alternative embodiment of the first support element 11 in a plan view. The two support elements 11, 13 are adjustable relative to each other by means of a helical gear which has a threaded spindle 15 and a thread 39 (not shown explicitly in FIGS. 16 and 17). The recess 35 provided to receive the threaded spindle 15 is arranged approximately centrally in the second support element 13.

In contrast to the first illustrative embodiment already described with reference to FIGS. 1 to 15, the support elements 11, 13 of the second illustrative embodiment, shown in FIGS. 16 and 17, have no intricate inner channel structure. The first and the second support element 11, 13 have relatively large cavities 42, which are arranged offset toward one end and have an oval cross section and form openings on the contact surfaces 25, 33. The openings formed by the cavities 42 take up slightly less than 50% of the contact surface 25, 33. The contact surfaces 25, 33 have a corrugated surface structure with a plurality of ribs 44 extending parallel to each other.

The cavities 42 are arranged lying opposite each other in the assembled state of the intervertebral implant 100, such that they form a continuous hollow space in the direction of the vertical axis H, at least in typical adjustment positions.

In other respects, the second illustrative embodiment corresponds substantially to the first illustrative embodiment already described with reference to FIGS. 1 to 15, and therefore reference is made to the description of said figures.

Figure 19:
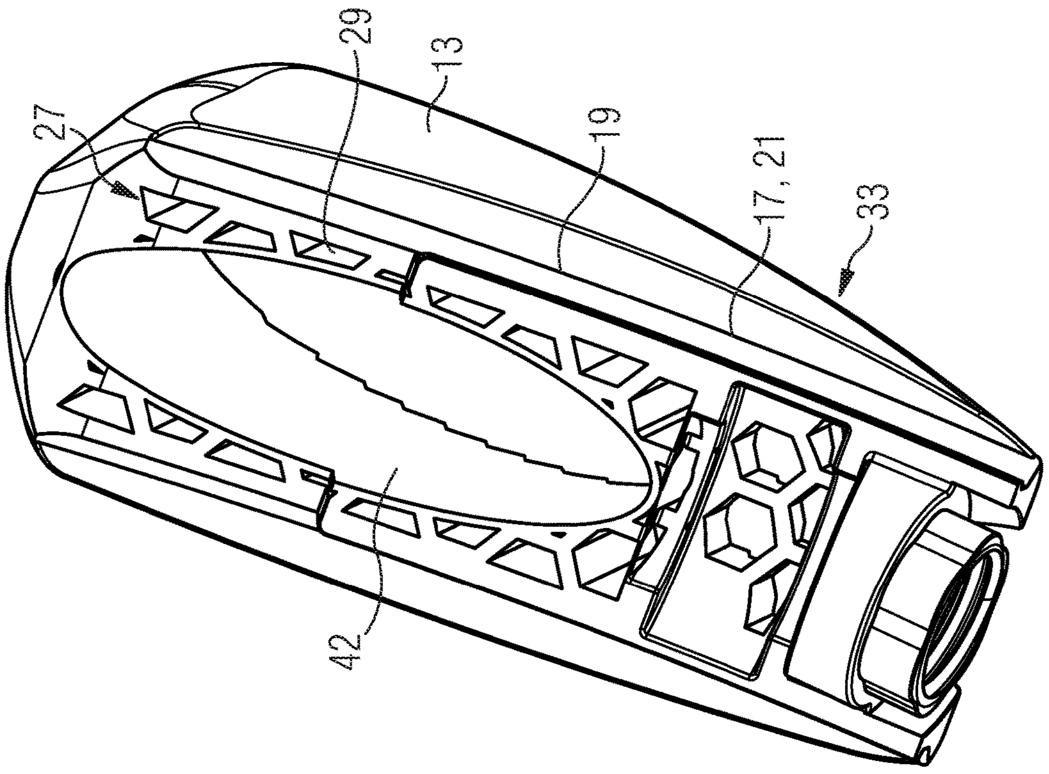
FIG. 19 is a perspective view of the support element of the third illustrative embodiment.
Figure 18:
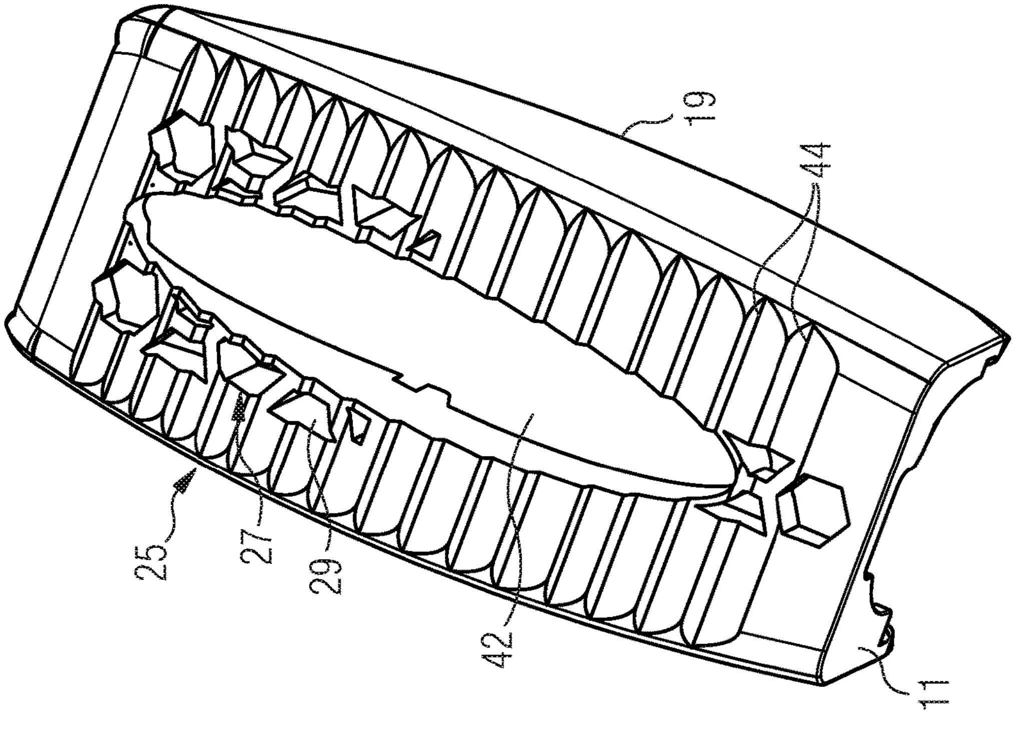
FIG. 18 is a perspective view of the support element of a third illustrative embodiment.

FIGS. 18 and 19 show a further illustrative embodiment of the intervertebral implant 100 according to the invention, which embodiment is structurally similar to the first illustrative embodiment and also to the second illustrative embodiment of FIGS. 16 and 17. The first and the second support element 11, 13 of the third illustrative embodiment shown by way of example each have an elongate and substantially centrally arranged cavity 42 with an oval shape. The openings formed by the cavities 42 take up approximately 30% of the contact surface 25, 33. The two cavities 42 of the first and the second support element 11, 13 at least partially overlap each other in typical angle settings of the two support elements 11, 13, such that a hollow space is formed that is continuous along the vertical axis. In addition, smaller inner channels 29 are provided which likewise promote penetration or inward growth of bone substance in the implanted state.

The recess 35 for the threaded spindle 15 (not shown explicitly in FIGS. 18 and 19) is arranged offset toward the end.

In other respects, the third illustrative embodiment corresponds substantially to the first illustrative embodiment and second illustrative embodiment already described, and therefore reference is made to the description of said embodiments.

The size of the cavities 42, in particular in the second and the third illustrative embodiment, is to be understood purely by way of example, in other illustrative embodiments, the cavities 42 can be greater or smaller and in particular can form openings on the respective contact surfaces 25, 33 of the corresponding support element 11, 13, which openings extend over at least 1/10 and at most 3/4 of the respective contact surface 25, 33.

In a fourth illustrative embodiment, the two support elements 11, 13 adjusted relative to each other are locked by means of an irreversible latch mechanism.

Figure 21:
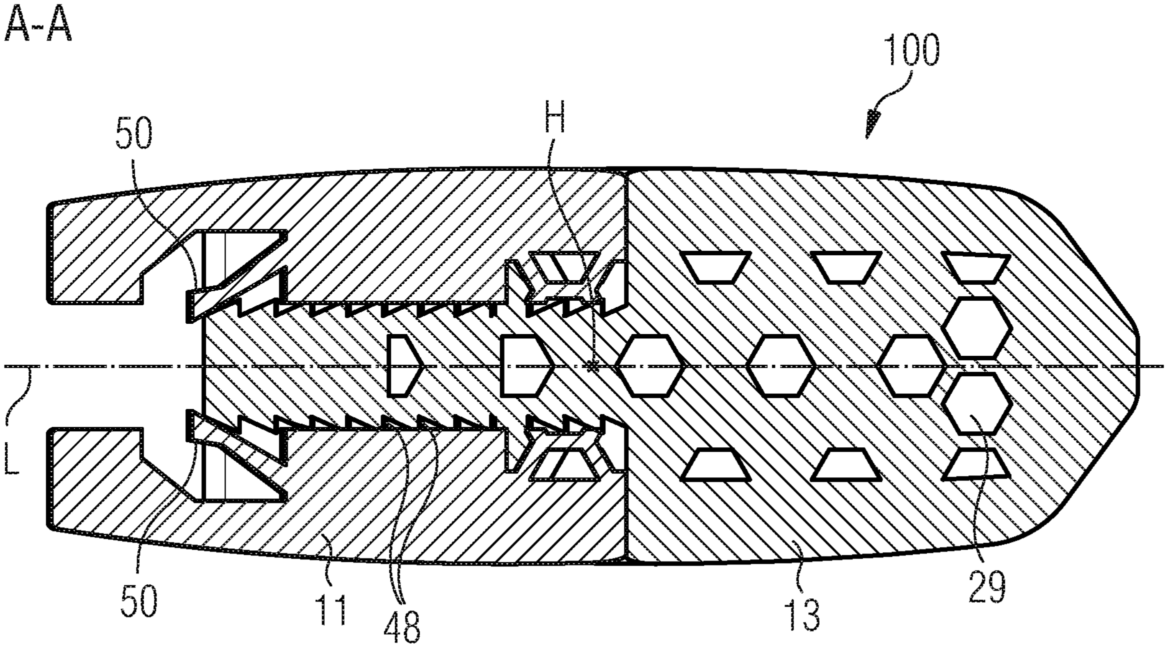
FIG. 21 is a sectional view of the intervertebral implant of the fourth illustrative embodiment.

The latch mechanism of the fourth illustrative embodiment contains a ridge 46 which limits the movement of the two support elements 11, 13 substantially to a translation along the circular arc contour 19 and in this sense assumes the function of the guide 17. The ridge 46 extends like a raised step over a central region of the inner face of the second support element 13 and contains a multiplicity of latch grooves 48 which are arranged laterally on opposite sides and into which latch arms 50 of complementary shape can engage in order to lock the first and the second support element 11, 13 at predefined positions. As can be seen in particular from the sectional view in FIG. 21, the latch arms 50 are arranged inwardly on the first support element 11 and are deflectable in a lateral direction, such that the first and the second support element 11, 13 can be adjusted relative to each other by a simple relative movement along the circular arc contour 19. The latch grooves 48 have substantially a triangular cross section with a steep flank and a gentle flank. The gentle flank is oriented in the direction of the circular arc contour 19 in such a way that the first and the second support element 11, 13 can be adjusted relative to each other, in particular in a direction toward greater angles and spacings of the contact surfaces 25, 33. The steep flank of the latch grooves 48 is oriented in the opposite direction, in particular in order to counteract a return movement of the latch arms 50, and therefore of the support elements 11, 13 adjusted relative to each other, for example under a load acting in the longitudinal direction of the spinal column.

Figure 20:
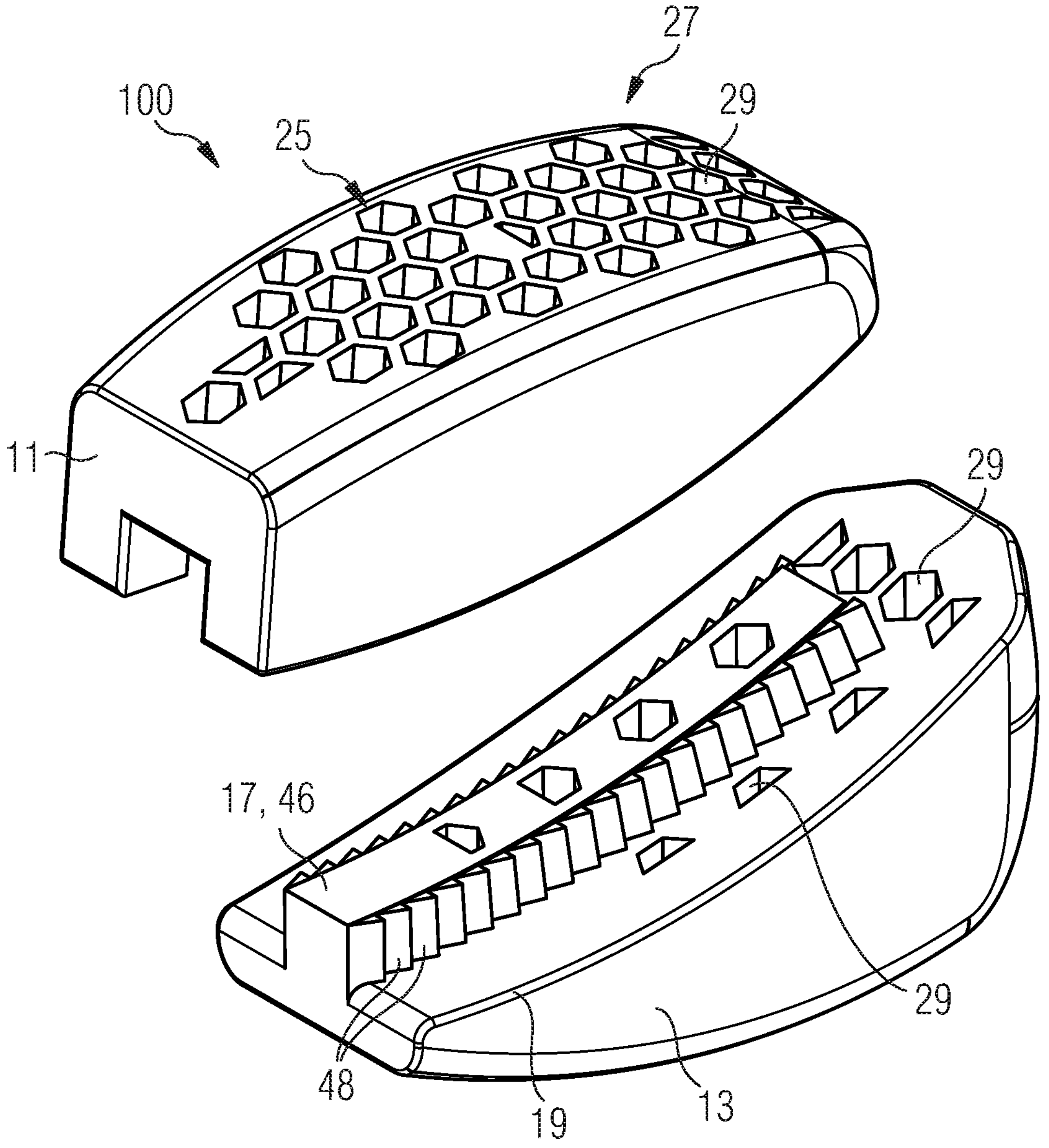
FIG. 20 is an exploded, perspective view of an intervertebral implant of a fourth illustrative embodiment with a latch mechanism.

The contact surfaces 25, 33 of the support elements 11, 13 are substantially smooth (cf. in particular FIG. 20) and bulge outward in a convex shape.

For the rest, reference is made to the above description, in particular in relation to FIGS. 1 to 17.

In a method for implanting the above-described intervertebral implant 100, the latter is preferably inserted via a dorsal access route into a region located between two vertebral bodies of the spinal column, if appropriate after removal of intervertebral disk material. The intervertebral implant 100 is advantageously inserted in a collapsed state, as is illustrated schematically in FIG. 3 for example, such that only a minimal access is required. The intervertebral implant 100 is arranged in the region located between the two vertebral bodies in such a way that the vertical axis H is oriented in the direction of the longitudinal axis of the spinal column, and the two contact surfaces 25, 33 are each oriented in the direction of the opposite vertebral bodies. The two support elements 11, 13 are then adjusted in such a way that the two contact surfaces 25, 33 bear on the two vertebral bodies at least in some regions, preferably over as large a surface area as possible. The spacing and the orientation of the two contact surfaces 25, 33 relative to each other are preferably adapted such that they correspond to the orientation and the spacing of the two vertebral bodies that are to be bridged. For this purpose, particularly in an intervertebral implant 100 according to the first illustrative embodiment, an implantation tool is inserted through the insertion opening 41 into the threaded spindle 15 and is then rotated.

Then, in particular after removal of the implantation tool, the intervertebral implant 100 is optionally filled at least partially with artificial bone substitute material in order to counteract sinking of the intervertebral implant 100 in the natural bone substance.

Although the invention has been set out and described in detail with reference to the preferred illustrative embodiments, the invention is not limited thereto. Other variations and combinations may be derived from these by a person skilled in the art, without in so doing departing from the essential concept of the invention. In particular, any desired combinations of features are possible that have been described or disclosed with reference to different illustrative embodiments and/or figures.

For example, it is obvious to a person skilled in the art to vary the profile of the circular arc contour 19 in respect of radius of curvature and/or inclination, for example in order to adapt the adjustability of the intervertebral implant 100, as regards the spacing and/or the orientation of the two contact surfaces 25, 33 relative to each other, in accordance with the associated variation in length. Many variations are also possible as regards the outer configuration of the intervertebral implant 100, without departing from the core concept of the invention.

LIST OF REFERENCE SIGNS

11 first support element
13 second support element
15 threaded spindle
16 outer contour
17 guide
19 circular arc contour
21 groove
23 projection
25 contact surface
26 inner face
27 structure
29 channel
31 channel wall
33 contact surface
34 inner face
35 recess
36 spindle seat
37 outer thread
38 inner thread
39 thread
41 insertion opening
42 cavity
44 ribs
46 ridge
48 latch groove
50 latch arm
100 intervertebral implant
L longitudinal axis
H vertical axis

The invention claimed is:

1. An intervertebral implant, comprising:

two support elements;

two opposite contact surfaces configured to bear at least regionally on vertebral bodies and are spaced apart from each other along a vertical axis and are each disposed on one of said two support elements;

said two support elements being adjustable relative to each other along a common circular arc contour and lockable relative to each other at least at predefined positions, said two support elements being displaceably guided relative to each other along the common circular arc contour while always bearing closely on each other along the circular arc contour with a constant radius of curvature and oriented on a longitudinal axis extending perpendicular to the vertical axis in such a way that, by adjustment of said two support elements relative to each other along said circular arc contour, a spacing of said two opposite contact surfaces with respect to the vertical axis and an angle setting of said two opposite contact surfaces relative to each other and with respect to the vertical axis can be predefined and/or modified.

2. The intervertebral implant as claimed in claim 1, wherein at least one of said two support elements has an inner structure with a plurality of channels which are open to said contact surface and which each have a cross-sectional area of 8,000 $\mu m^2$ to 7,000,000 $\mu m^2$.

3. The intervertebral implant according to claim 1, wherein both of said opposite contact surfaces disposed opposite each other each have an inner structure which each contain a plurality of channels, wherein said inner structures which are disposed opposite each other form, in at least one part of the intervertebral implant, at least one continuous hollow space in a direction of the vertical axis.

4. The intervertebral implant according to claim 2, wherein said inner structure is honeycomb-shaped, lattice-shaped or mesh-shaped.

5. The intervertebral implant according to claim 2, wherein said channels have a round or oval cross section or a cross section in a shape of a polygon, a triangular, a rectangular, a square or a hexagonal.

6. The intervertebral implant according to claim 1, wherein at least one of said two support elements has at least one cavity formed therein which forms an opening on said contact surface of said at least one support element, an area of said opening extends at least over 1/10 and at most 3/4 of said contact surface of said at least one support element.

7. The intervertebral implant according to claim 6, wherein both of said opposite contact surfaces disposed opposite each other has in each case at least one cavity formed therein, said cavities being disposed opposite each other in such a way that said cavities in at least one part of the intervertebral implant form at least one continuous hollow space in a direction of the vertical axis.

8. The intervertebral implant according to claim 1, wherein at least one of said opposite contact surfaces has a convex bulge.

9. The intervertebral implant according to claim 1, further comprising an adjustment mechanism, said two support elements having said opposite contact surfaces are adjustable relative to each other by means of said adjustment mechanism.

10. The intervertebral implant according to claim 1, further comprising an adjustment mechanism, said two support elements having said opposite contact surfaces are lockable relative to each other by means of said adjustment mechanism.

11. The intervertebral implant according to claim 9, wherein said adjustment mechanism is a reversible adjustment mechanism.

12. The intervertebral implant according to claim 9, wherein said adjustment mechanism is an irreversible adjustment mechanism.

13. The intervertebral implant according to claim 11, wherein said reversible adjustment mechanism is configured as a helical gear and has a threaded spindle guided in a thread.

14. The intervertebral implant according to claim 13, wherein said thread is introduced in one of said two support elements and has a curvature corresponding to a curvature of said circular arc contour.

15. The intervertebral implant according to claim 13, wherein said threaded spindle is insertable into a spindle seat that inhibits a rotation movement.

16. The intervertebral implant according to claim 9, wherein said adjustment mechanism is configured as a latch mechanism.

17. The intervertebral implant according to claim 16, wherein a first of said two support elements contains at least one deflectable latch arm, and a second of said two support elements contains a plurality of latch grooves spaced apart from each other along said circular arc contour, wherein said deflectable latch arm is configured to latch into said latch grooves, said at least one deflectable latch arm and said latch grooves form said adjustment mechanism.

18. A method for producing an intervertebral implant, which comprises the steps of:

producing the intervertebral implant by means of a generative production method; and forming the intervertebral implant to have two opposite contact surfaces configured to bear at least regionally on vertebral bodies and being spaced apart from each other along a vertical axis and are each disposed on support elements being adjustable relative to each other along a common circular arc contour and lockable relative to each other at least at predefined positions, the support elements being displaceably guided relative to each other along the common circular arc contour while always bearing closely on each other along the circular arch contour with a constant radius of curvature and oriented on a longitudinal axis extending perpendicular to the vertical axis in such a way that, by adjustment of the support elements relative to each other along the circular arc contour, a spacing of the two opposite contact surfaces with respect to the vertical axis and an angle setting of the two opposite contact surfaces relative to each other and with respect to the vertical axis can be predefined and/or modified.

19. A method for implanting an intervertebral implant, which comprises the steps of:

making available the intervertebral implant having two opposite contact surfaces configured to bear at least regionally on vertebral bodies and are spaced apart from each other along a vertical axis and are each disposed on two support elements which are adjustable relative to each other along a common circular arc contour and lockable relative to each other at least at predefined positions, the two support elements being displaceably guided relative to each other along the common circular arc contour while always bearing closely on each other along the circular arc contour with a constant radius of curvature and oriented on a longitudinal axis extending perpendicular to the vertical axis in such a way that, by adjustment of the two support elements relative to each other along the circular arc contour, a spacing of the two opposite contact surfaces with respect to the vertical axis and an angle setting of the two opposite contact surfaces relative to each other and with respect to the vertical axis can be predefined and/or modified;

making available an access route to a region located between two opposite vertebral bodies of a spinal column;

inserting the intervertebral implant in a collapsed state into the region located between the two opposite vertebral bodies, in such a way that the vertical axis of the intervertebral implant is oriented in a direction of the longitudinal axis of the spinal column, and the two opposite contact surfaces are each oriented in a direction of the two opposite vertebral bodies; and adjusting the two support elements relative to each other along the circular arc contour in such a way that the two opposite contact surfaces bear at least regionally on the two opposite vertebral bodies.

20. The implantation method according to claim 19, wherein the intervertebral implant is filled at least partially with a bone substitute material.

* * * * *